United States Patent [19]

O'Neill et al.

[11] 3,966,450

[45] June 29, 1976

[54] ANIMAL WASTE ODOR TREATMENT

[75] Inventors: Eugene T. O'Neill, Hightstown; William H. Kibbel, Jr., Pennington, both of N.J.

[73] Assignee: FMC Corporation, Philadelphia, Pa.

[22] Filed: Aug. 12, 1974

[21] Appl. No.: 496,518

[52] U.S. Cl. .................................. 71/15; 71/37; 210/63 R
[51] Int. Cl.² .................. C05F 3/00; C02C 1/40
[58] Field of Search ............... 71/11, 15, 20, 21, 37, 71/38, 39, 40, 41; 210/18, 63, 64

[56] References Cited
UNITED STATES PATENTS

| 3,050,383 | 9/1962 | Wilson | 71/21 X |
|---|---|---|---|
| 3,705,098 | 12/1972 | Shepherd | 210/63 |

OTHER PUBLICATIONS

The Control of Sulphides in Sewerage Systems, Thistlethwayte, Ed., Ann Arbor Science Pub. Inc., 1972.

Process Design Manual for Sulfide Control in Sanitary Sewage Systems, U.S. EPA, 1974.

Primary Examiner—Charles N. Hart
Assistant Examiner—Ferris H. Lander

[57] ABSTRACT

Controlling the odor of an animal waste slurry and increasing the plant nutrient values in said animal waste slurry is achieved by contacting an animal waste slurry with about 5 ppm to about 500 ppm hydrogen peroxide, adjusting the pH of the slurry to between about 4.0 and about 8.0 with a mineral acid, mixing the slurry until the odor is no longer objectionable, and recovering the animal waste slurry which contains increased amounts of ammonium salt values.

5 Claims, No Drawings

ANIMAL WASTE ODOR TREATMENT

This invention relates to the treatment of animal waste slurries. In particular, it is concerned with the removal of odorous and noxious gases emanating from animal waste slurries present in storage pits or tanks and with increasing the plant nutrient values in the animal waste.

In recent years the raising of animals in confined areas such as feedlots and similar high animal concentration facilities has become commonplace. This trend is a result of several factors, including increased technology in the livestock industry, and increased population and weight gain of confined animals over pasture and yard animals. A principal drawback of animal confinement raising is the intense odor emanated from the animal wastes which accumulate in the relatively small areas occupied by the animals. Until relatively recently, animal waste odors have not been a problem because the enterprises raising the animals were located at some distance from residential communities, and hence odor dilution by the prevailing winds was adequate. Urban growth, however, has put residential communities much nearer to the animal enterprises and the same odors previously ignored or unnoticed are now offensive and a serious problem.

Numerous procedures have been developed to physically dispose of the animal wastes. Some of these include solid or slurry spreading on fields, oxidation ditches, incineration, and anerobic or aerobic lagoons or digestion systems. Except for field spreading, these treatments involve significant capital expense and/or operating expenditures. Furthermore, these procedures do not eliminate the objectionable odors evolved from the animal wastes except in the aerobic treatment process.

Numerous procedures or systems for dealing with animal waste odors have also been developed. Some involve the use of specifically designed water scrubbers located in the ventilating system of a confinement area. Other procedures involve masking the odors with various scents; oxidizing the odors with oxidizing chemicals such as ammonium persulfate; and selectively inhibiting the formation of the odorous compounds with sulfa drugs.

An efficient and economic process has been unexpectedly discovered for controlling the odor of an animal waste slurry and increasing the plant nutrient values in the animal waste slurry by contacting the animal waste slurry with about 5 ppm to about 500 ppm hydrogen peroxide as an aqueous hydrogen peroxide solution; adjusting the pH of the slurry to between about 4.0 and about 8.0 with a mineral acid selected from the group consisting of phosphoric acid, sulfuric acid, and nitric acid; mixing the slurry until the animal waste odor is no longer objectionable; and recovering a treated animal waste slurry containing increased amounts of ammonium salts selected from the group consisting of ammonium phosphate salts, ammonium sulfate salts, and ammonium nitrate.

The odors in animal waste slurries are generally noxious gases produced by anaerobic microbial decomposition of organic material present in the waste. The noxious gases include ammonia, hydrogen sulfide, methane, and trace quantities of numerous organic compounds such as mercaptans and skatole. Treatment of an animal waste slurry according to the invention results in the formation of an odor free animal waste slurry, remaining odor free for several hours, which can be removed and transported from the confinement area or other collection point to a disposal zone such as an open field or a compost station. The treated animal waste slurry is preferably spread as a fertilizer in view of the increased plant nutrient values present in the slurry.

In the process of this invention an animal waste slurry is contacted with an aqueous hydrogen peroxide solution and a mineral acid. The slurry preferably contains about 5% to 25% solids although other pumpable consistencies may be employed.

The aqueous hydrogen peroxide solution is preferably a dilute solution of hydrogen peroxide, containing from 5% to 50% hydrogen peroxide. The amount of hydrogen peroxide necessary to control the unpleasant odors depends upon such factors as the kind of animal waste; feed, age, temperature, and consistency of the animal waste; and the degree of aeration. Higher amounts of peroxide are needed with poultry waste; waste stored for long times in storage pits or tanks; warm temperature waste; and nonaerated waste. Lower amounts of peroxide are effective with horse, cattle, goat, and swine wastes; fresh waste accumulations; cool temperature waste; and aerated waste. In general, about 5 ppm to about 500 ppm, and preferably about 50 ppm to about 200 ppm hydrogen peroxide (100% $H_2O_2$ basis) based on the volume of the animal waste slurry is sufficient to eliminate substantially all of the oxidizable sulfides and other sulfurous odors.

The mineral acids employed in the invention are phosphoric acid, sulfuric acid and nitric acid. The acids may be used singly or used in combination with one another. The mineral acids are added to the animal waste slurry in amounts sufficient to control the ammonia and related amine odors prominent in animal waste slurries which are not responsive to hydrogen peroxide treatment. This is accomplished by adjusting the pH of the slurry to between about 4.0 and about 8.0 with of mineral acid. Within the pH range ammonium salt formation occurs and hydrogen peroxide decomposition is limited. When the mineral acid is phosphoric acid, the pH of the slurry is preferably adjusted to between about 4.5 and about 7.5. Within this pH range, the ammonium phosphate salts which are formed in varying amounts are monoammonium orthophosphate ($NH_4H_2PO_4$), diammonium orthophosphate (($NH_4)_2HPO_4$), and triammonium orthophosphate (($NH_4)_3PO_4.3H_2O$). When the mineral acid is sulfuric acid, the pH of the slurry is preferably adjusted to between about 5.0 and about 7.0. Within this pH range, the ammonium sulfate salts which are formed in varying amounts are ammonium bisulfate ($NH_4HSO_4$), and ammonium sulfate (($NH_4)_2SO_4$). When the mineral acid is nitric acid, the pH of the slurry is preferably adjusted to between about 3.5 and 5.5. Within this pH range ammonium nitrate is formed. When combinations of the mineral acids are used, combinations of the ammonium salts are formed. For example, the use of phosphoric acid and sulfuric acid will result in the formation of ammonium phosphate salts and ammonium sulfate salts.

The formation of these ammonium salts within the animal waste slurry prevents the evolution of ammonia and related amine odors from the animal waste slurry and increases the plant nutrient value of the animal waste slurry.

3

The aqueous hydrogen peroxide solution and mineral acid are added to the animal waste slurry either simultaneously or separately. In aqueous solutions containing hydrogen peroxide and a mineral acid which are stored for extended periods of time prior to use, phosphoric acid is the preferred mineral acid for maximum hydrogen peroxide stability. Preferably the slurry is mixed by conventional means while the slurry is being treated, with mixing continuing until the animal waste odor is no longer objectionable.

Hydrogen peroxide can be used either in the free state or combined as the peroxyhydrates of inorganic salts which break down in aqueous media to yield hydrogen peroxide. Examples of such salts are sodium metaborate peroxyhydrate and sodium carbonate peroxide. It is preferred to use the free state of hydrogen peroxide since it breaks down into water and oxygen and does not leave any foreign residue in the slurry to contaminate the environment.

The aqueous hydrogen peroxide solution may be optionally stabilized by conventional methods, such as by employing magnesium oxide or other stabilizers in the aqueous hydrogen peroxide solution. Likewise, conventional metal catalysts may also be employed to assist in the oxidation reaction. These catalysts include salts of iron, cobalt, nickel, copper, manganese, molybdenum, and vanadium with the iron salts preferred.

The following examples are given to illustrate the invention but are not deemed limiting thereof. All percentages given are based upon total weight unless otherwise indicated and parts per million (ppm) are based on total slurry volume.

EXAMPLE 1

A 4 l sample of a chicken manure slurry containing about 20% solids was removed from a 7,200 gallon slurry holding tank located outside a chicken confinement house and carefully poured into a calibrated polyethylene container to prevent aeration. The sample was then subjected to treatment with various amounts of hydrogen peroxide and phosphoric acid. After the sample was contacted with the chemical treating agent, the sample was mixed mechanically for about 15 minutes. After mixing, the atmosphere above the sample was analyzed for $H_2S$ (hydrogen sulfide) and $NH_3$ (ammonia) using a gas detector test kit. The pH of the slurry was analyzed with a Bechman pH meter and the amount of solution sulfides, that is, hydrogen sulfide and dissolved sulfides was determined. Odor characteristics were evaluated subjectively by smell.

Comparative Runs A and B

In Run A, the slurry was mixed for 15 minutes in the absence of hydrogen peroxide and phosphoric acid.

In Run B, the slurry of Run A was contacted with 55.8 ml of a 1% $H_2O_2$ solution (100 ppm).

Process of the Invention — Runs 1 to 5

In Run 1, the slurry of Run B containing 100 ppm $H_2O_2$ was contacted with 55.8 ml of a 1% $H_3PO_4$ solution (100 ppm).

In Runs 2 and 3 additional amounts of a 1% $H_3PO_4$ solution were added to the slurry of Run 1 to increase the acid concentration in the slurry to 500 ppm and 1,033 ppm respectively.

In Run 4, the slurry of Run 3 containing 100 ppm $H_2O_2$ and 1,033 ppm $H_3PO_4$ was contacted with an additional amount of $H_2O_2$ (1% solution) to increase the hydrogen peroxide concentration to 200 ppm.

In Run 5, a 4 l sample of a chicken manure slurry was contacted with 500 ppm $H_2O_2$ (1% solution) and 1,063 ppm $H_3PO_4$ (1% solution).

In each of the runs, the slurry was mixed for 15 minutes after addition of the treating agent and then analyzed as described above. The results are set forth in Table I.

Prior to hydrogen peroxide addition (Run A) the slurry sulfide concentration was 5mg/l and the atmosphere above the slurry had a strong hydrogen sulfide, ammonia and skatole odor. After the initial hydrogen peroxide addition (Run B) the slurry sulfide concentration dropped very sharply to 0.1 mg/l but the atmosphere above the slurry had a strong ammonia and skatole odor indicating incomplete oxidation of skatole and the amine compounds. The slurries treated with both hydrogen peroxide and phosphoric acid (Runs 1 to 5) showed a complete absence of slurry sulfides. The atmosphere above the slurries also showed a complete absence of hydrogen sulfide, a slight ammonia odor, and a skatole odor. The slurries recovered from Runs 1 to 5 had an increased ammonium and phosphate content resulting from the formation of ammonium phosphate salts.

EXAMPLE 2

The procedure set forth in Example 1 was repeated in the following runs.

Comparative Run C

In Run C, a 4 l sample of a chicken manure slurry was contacted with 200 ppm $H_2O_2$ (1% solution), and 200 ppm Fe ion (ferrous sulfate solution).

Process of the Invention — Runs 6 to 9

In Run 6, a 4 l sample of a chicken manure slurry was contacted with 200 ppm $H_2O_2$ (1% solution), and 3,613 ppm $H_3PO_4$ (1% solution).

In Run 7, a 4 l sample of a chicken manure slurry was contacted with 200 ppm $H_2O_2$ (1% solution) and 1,467 ppm $H_2SO_4$ (1% solution).

In Run 8, a 4 l sample of a chicken manure slurry was contacted with 200 ppm $H_2O_2$ (1% solution), 1,490 ppm $H_2SO_4$ (1% solution) and 200 ppm Fe ion (ferrous sulfate solution).

In Run 9, a 4 l sample of a chicken manure slurry was contacted with 200 ppm $H_2O_2$ (1% solution), 1,488 ppm $H_3PO_4$ (1% solution), and 200 ppm Fe ion (ferrous sulfate solution).

In each of the runs, the slurry was mixed for 15 minutes after addition of the treating agent and then analyzed as described in Example 1. The results are set forth in Table II.

Comparative Run C demonstrates that a slurry treated with hydrogen peroxide and a catalytic amount of iron salt for 15 minutes is completely absent of slurry sulfides and atmospheric hydrogen sulfide odors. This treatment alone, however, is not sufficient to eliminate the ammonia and skatole odors. Inventive Run 6 demonstrates that a slurry treated for only 15 minutes with hydrogen peroxide and phosphoric acid is completely absent of slurry sulfides, and atmospheric hydrogen sulfide, ammonia and skatole odors. Inventive Run 7 demonstrates that a slurry treated for only 15 minutes with hydrogen peroxide and sulfuric acid is completely absent of slurry sulfides and atmospheric hydrogen sulfide odor. The atmosphere also had a sharply dropped ammonia concentration. Inventive Run 8 demonstrates that a slurry treated for only 15 minutes with hydrogen peroxide, sulfuric acid and a catalytic amount of iron salt is completely absent of slurry sulfides and atmospheric hydrogen sulfide, ammonia and skatole odors. Inventive Run 9 demonstrates that a slurry treated for only 15 minutes with hydrogen peroxide, phosphoric acid and a catalytic amount of iron salt is completely absent of slurry sulfides and atmospheric hydrogen sulfide. The atmosphere also had a sharply decreased ammonia concentration.

The invention being thus described, it will be obvious that the same may be varied in many ways. Such variations are not to be regarded as a departure from the scope and the spirit of the invention, and all such modifications are intended to be included within the scope of the following claims.

TABLE I

| Example 1 | Treating Agent (ppm) | | Slurry | Atmosphere (ppm) | | Odor |
| | $H_2O_2$ | $H_3PO_4$ | pH | Sulfides (mg/l) | $H_2S$ | $NH_3$ | |
| --- | --- | --- | --- | --- | --- | --- | --- |
| Comparative | | | | | | | |
| Run A | 0 | 0 | 7.15 | 5 | 410 | 15 | Strong $H_2S$, $NH_3$, skatole |
| Run B | 100 | 0 | 7.15 | 0.1 | 6 | 8 | Strong $NH_3$, skatole |
| Inventive | | | | | | | |
| Run 1 | 100 | 100 | 7.10 | 0 | 0 | 2.5 | Strong skatole |
| Run 2 | 100 | 500 | 7.00 | 0 | 0 | 1 | Strong skatole |
| Run 3 | 100 | 1033 | 6.50 | 0 | 0 | 0 | Skatole |
| Run 4 | 200 | 1033 | 6.50 | 0 | 0 | 0 | Slight skatole, animal |
| Run 5 | 500 | 1063 | 6.50 | 0 | 0 | 0 | Slight skatole |

TABLE II

| Example 2 | Treating Agent (ppm) | | | | | Slurry Sulfides (mg/l) | Atmosphere (ppm) | | Odor |
| | $H_2O_2$ | $H_3PO_4$ | $H_2SO_4$ | Fe | pH | | $H_2S$ | $NH_3$ | |
| --- | --- | --- | --- | --- | --- | --- | --- | --- | --- |
| Comparative | | | | | | | | | |
| Run C | 200 | 0 | 0 | 200 | 7.20 | 0 | 0 | 16 | Strong $NH_3$, skatole |
| Inventive | | | | | | | | | |
| Run 6 | 200 | 3613 | 0 | 0 | 6.25 | 0 | 0 | 0 | Slight animal, musty |
| Run 7 | 200 | 0 | 1467 | 0 | 6.50 | 0 | 0 | 2 | $NH_3$, skatole |
| Run 8 | 200 | 0 | 1490 | 200 | 6.50 | 0 | 0 | <1 | Silage, animal |
| Run 9 | 200 | 1488 | 0 | 200 | 6.50 | 0 | 0 | 1 | $NH_3$, skatole |

<means "less than"

What is claimed is:

1. A process for simultaneously controlling the odor of an animal waste slurry and increasing the plant nutrient values in said animal waste slurry, which comprises:

contacting an animal waste slurry with about 5 ppm to about 500 ppm hydrogen peroxide as an aqueous hydrogen peroxide solution based on 100% hydrogen peroxide;

adjusting the pH of the slurry to between about 4.0 and about 8.0 with a mineral acid selected from the group consisting of phosphoric acid, sulfuric acid, and nitric acid;

mixing the slurry until the animal waste odor is no longer objectionable whereby ammonia and related amine odors are converted into ammonium salts; and recovering a treated animal waste slurry containing increased amounts of ammonium salts selected from the group consisting of ammonium phosphate salts, ammonium sulfate salts, and ammonium nitrate.

2. The process of claim 1 wherein the pH of the slurry is adjusted to between about 4.5 and about 7.5 with phosphoric acid and the ammonium phosphate salt values are increased in said slurry.

3. The process of claim 1 wherein the pH of the slurry is adjusted to between about 5.0 and about 7.0 with sulfuric acid and the ammonium sulfate salt values are increased in said slurry.

4. The process of claim 1 wherein the pH of the slurry is adjusted to between about 3.5 and about 5.5 with nitric acid and the ammonium nitrate values are increased in said slurry.

5. The process of claim 1 wherein the slurry is contacted with about 50 ppm to about 200 ppm hydrogen peroxide as an aqueous hydrogen peroxide solution.

* * * * *